(12) United States Patent
Yoo et al.

(10) Patent No.: US 8,696,126 B2
(45) Date of Patent: *Apr. 15, 2014

(54) EYE AND BODY MOVEMENT TRACKING FOR TESTING AND/OR TRAINING

(75) Inventors: Herb Yoo, Beaverton, OR (US); Alan W. Reichow, Beaverton, OR (US)

(73) Assignee: Nike, Inc., Beaverton, OR (US)

( * ) Notice: Subject to any disclaimer, the term of this patent is extended or adjusted under 35 U.S.C. 154(b) by 166 days.

This patent is subject to a terminal disclaimer.

(21) Appl. No.: 13/333,449

(22) Filed: Dec. 21, 2011

(65) Prior Publication Data

US 2012/0092618 A1    Apr. 19, 2012

Related U.S. Application Data

(63) Continuation of application No. 12/500,368, filed on Jul. 9, 2009, now Pat. No. 8,100,532.

(51) Int. Cl.
*A61B 3/14* (2006.01)

(52) U.S. Cl.
USPC ............................. 351/209; 351/210; 351/206

(58) Field of Classification Search
USPC .................................................. 351/200–246
See application file for complete search history.

(56) References Cited

U.S. PATENT DOCUMENTS

| | | | |
|---|---|---|---|
| 3,861,790 A | 1/1975 | Tamura | |
| 4,950,069 A | 8/1990 | Hutchinson | |
| 5,050,982 A | 9/1991 | Meissner | |
| 5,173,724 A | 12/1992 | Bonham | |
| 5,478,239 A | 12/1995 | Fuerst | |
| 6,386,706 B1 * | 5/2002 | McClure et al. | 351/237 |
| 6,755,525 B2 | 6/2004 | Reichow | |
| 6,811,258 B1 | 11/2004 | Grant | |
| 6,893,127 B2 | 5/2005 | Reichow | |
| 6,960,171 B2 * | 11/2005 | Sanders | 600/558 |
| 7,073,208 B2 | 7/2006 | Penque | |

(Continued)

FOREIGN PATENT DOCUMENTS

| | | |
|---|---|---|
| DE | 19707902 | 9/1999 |
| JP | 2004298461 | 10/2004 |

(Continued)

OTHER PUBLICATIONS

Reichow, et al., "Introduction to Behavioral Optometry", Sports Vision, 1993, 75 pages, Optometric Extension Program Foundation, United States, December.

(Continued)

*Primary Examiner* — Mohammed Hasan
(74) *Attorney, Agent, or Firm* — Shook, Hardy & Bacon L.L.P.

(57) ABSTRACT

The eye movement, body movement, and/or physiological performance of a subject may tracked while the subject performs a task, such as participating in an activity or sport. The collected data may then be used to identify correlations between the subject's eyesight and the subject's body movement exists and/or physiology. Such a correlation may be analyzed (e.g., over time) to determine any delays or gaps in the subject's ability to track an object, such as a ball, while participating in a sport or other activity. Further, a subject's performance may be compared to data collected from other individuals. The eye movement, body movement, and/or physiological performance data may be used to test and/or train the visual and cognitive abilities of an individual.

20 Claims, 9 Drawing Sheets

(56) References Cited

U.S. PATENT DOCUMENTS

| | | | |
|---|---|---|---|
| 7,306,335 | B2 | 12/2007 | Miyake |
| 7,515,054 | B2 * | 4/2009 | Torch .................... 340/573.1 |
| 8,100,532 | B2 * | 1/2012 | Yoo et al. ............... 351/209 |
| 2003/0153846 | A1 | 8/2003 | Marple-Horvat |

FOREIGN PATENT DOCUMENTS

| | | |
|---|---|---|
| JP | 2008295654 | 12/2008 |
| WO | 2005094667 | 10/2005 |
| WO | 2008128192 | 10/2008 |

OTHER PUBLICATIONS

Ferreira, "An Overview of Research in Sports Vision: its History and an Optometric Perspective", The South African Optometrist, Dec. 2003, pp. 142-149, vol. 62, No. 4, Auckland Park, South Africa.

Coffey, et al., "Visual Performance Enhancement in Sports Optometry", Sports Vision 1995, pp. 158-177, Butterworth-Heinermann, United States, December.

Cardall, "Contact Lenses in Sport: a General Overview", Optician, Jan. 13, 2006, pp. 22-25, vol. 231, No. 6034, United States.

Rouse, et al., "A Comparison Study of Dynamic Visual Acuity Between Athletes and Nonathletes", Journal of the American Optometric Association, Dec. 1988, pp. 946-950, vol. 59, No. 12, United States.

Koenig, "Practicing Perception: Eyes Can Be Trained to be More Effective", USA Today Baseball Weekly, 1996, 3 pages, United States, March.

Coffey, et al., "Optometric Evaluation of the Elite Athlete," Problems in Optometry, Mar. 1990, pp. 32-59, vol. 2, No. 1, United States.

Reichow, et al., "A Comparison of Contrast Sensitivity in Elite Athletes Versus a Normal Population", American Journal of Optometry and Physiological Optics, Dec. 15, 1986, vol. 63, No. 82, United States.

Farrow, et al., "An Investigation of the Effectiveness of Bolle's Competivision Sport-Glasses on Tennis Performance", Clinical and Experimental Optometry, Jul.-Aug. 2000, pp. 226-231, vol. 83, No. 4.

Herdman, et al., "Computerized Dynamic Visual Acuity Test in the Assessment of Vestibular Deficits", The American Journal of Otology, 1998, pp. 790-796, vol. 19, No. 6, United States.

Tian, et al., "Dynamic Visual Acuity During Transient and Sinusoidal Yaw Rotation in Normal Ulilaterally Vestibulopathic Humans", Experimental Brain Research, Feb. 8, 2001, pp. 12-25, vol. 137, Springer-Verlag, United States.

Reichow, et al., "Ultraviolet and Short Wavelength Visible Light Exposure: Why Ultraviolet Protection Alone is Not Adequate", Journal of Long-Term Effects of Medical Implants, 2006, pp. 315-325, vol. 16, No. 4, Begell House, Inc., United States.

International Search Report and Written Opinion for PCT/US2010/014565 filed Jul. 9, 2010.

Office Action of Jan. 5, 2011 for U.S. Appl. No. 12/500,368.

Office Action of Jun. 7, 2011 for U.S. Appl. No. 12/500,368.

Japanese Office Action of Jul. 9, 2013 for Application No. 2012-519773.

European Supplemental Search Report of Jul. 26, 2013 for Application No. 10797390.

* cited by examiner

EYE AND BODY MOVEMENT TRACKING FOR TESTING AND/OR TRAINING

CROSS-REFERENCE TO RELATED APPLICATIONS

This application is a continuation of U.S. patent application Ser. No. 12/500,368, filed on Jul. 9, 2009, now U.S. Pat. No. 8,100,532 B2 and entitled "EYE AND BODY MOVEMENT TRACKING FOR TESTING AND/OR TRAINING."

STATEMENT REGARDING FEDERALLY SPONSORED RESEARCH OR DEVELOPMENT

Not applicable.

TECHNICAL FIELD

The present invention relates to tracking and testing eye movements of a subject. More particularly, the present invention relates to correlated tracking and testing body movements and eye movements of a subject while performing a particular activity.

BACKGROUND

Tracking the eye movement of a subject while the subject is performing a particular activity or participating in a sport may provide beneficial information regarding the subject's visual tracking during the activity or sport. Collecting such data may not, however, reveal all deficiencies that the subject may have, for example, in tracking a baseball while attempting to hit the ball.

SUMMARY

In accordance with embodiments of the present invention, systems and methods for simultaneously testing and/or training a subject's body and eye movement are provided. The eye movement of a subject may be tracked, while the subject is participating in an activity or sport. Depending on the particular activity or sport, the movement of the subject may also be tracked while the subject is participating in the activity or sport. The tracking data, both from the subject's eye movement and body movement, may then be used to identify correlations between the subject's eye movements and angels of gaze and the subject's body movement exists. Further, physiological data may be collected from the subject while the subject is participating in the activity or sport, and that physiological data may be analyzed to identify correlations between the physiological data, the eye movement data, and/or the body movement data. Such a correlation may be analyzed over time to determine any delays or gaps in the subject's ability to perform a task associated with a sport or activity, such as catching a ball, that occurs while participating in a sport or other activity.

A variety of types of data may be collected and correlated in accordance with the present invention. Eye movement data may include, for example, measurements of pursuit, saccadic movements, focus, vergence, pupil dilation and constriction, etc. Body movement data may include gross body movements, fine body movements, movement of specific body parts (head, hands, feet, etc.), and the like. Physiological data may include balance data, and blood pressure, heart rate, etc. may also be collected, and correlated with the eye movement data and/or body movement data. Further, collected data may be compared and/or correlated in any number of ways.

The correlation and/or other analysis of data in accordance with the present invention may be useful for a variety of purposes. For example, the present invention may be used to identify the skill level of an individual relative to other individuals. By way of further example, the present invention may be used to identify areas of potential improvement for an individual. As yet a further example, the present invention may be used to identify optimal performance parameters and/or techniques for a given task by, for example, obtaining information as to how acknowledged successful/expert performers perform a task. For those seeking to improve their performance of a task, the present invention may be used to train and/or evaluate the progress of training. Further, the present invention may be used to test or train the cognitive and/or mental focus of an individual, as the eye movements of an individual often indicates the cognitive and/or mental focus of the individual. Of course, any number of uses may be made of systems and methods in accordance with the present invention.

It should be noted that this Summary is provided to generally introduce the reader to one or more select concepts described below in the Detailed Description in a simplified form. This Summary is not intended to identify key and/or required features of the claimed subject matter, nor is it intended to be used as an aid in determining the scope of the claimed subject matter.

BRIEF DESCRIPTION OF THE DRAWINGS

The present invention is described in detail below with reference to the attached drawing figures, wherein.

DETAILED DESCRIPTION

Figure 1:
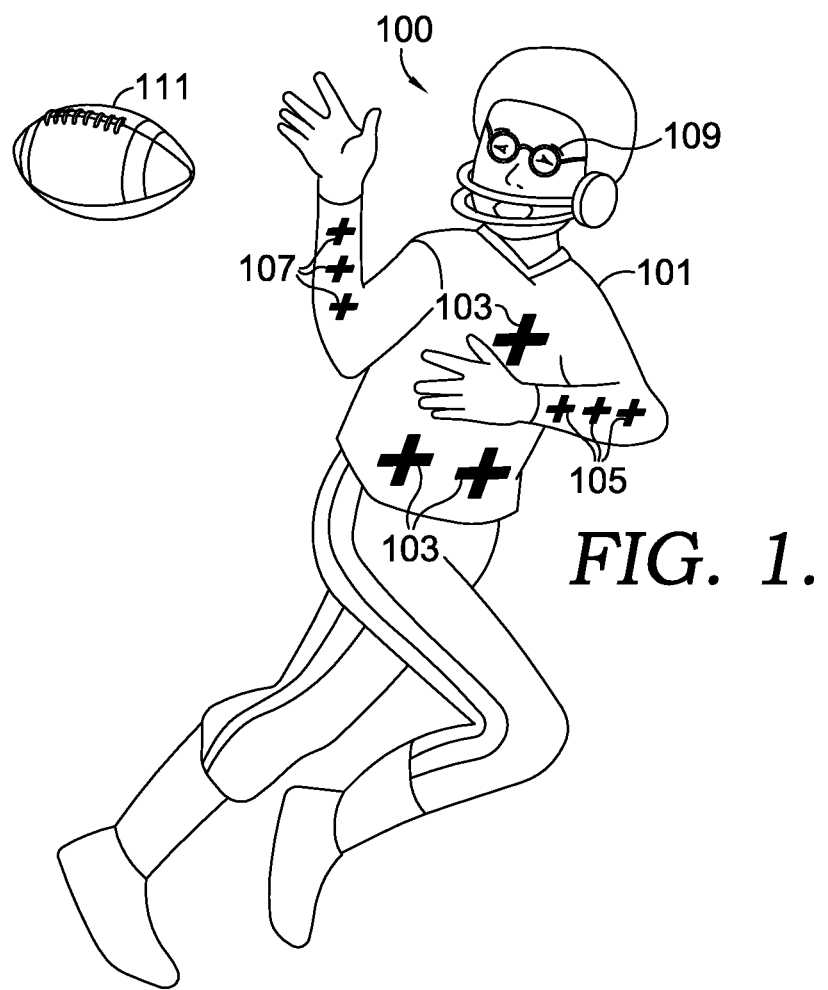
FIG. 1 illustrates an embodiment of a system for evaluating the performance of an individual in accordance with the present invention.

In general, a subject may perform activities or tasks specific to the particular sport or activity the subject is involved in. For example, if a subject participated in baseball, subject's hands may be tracked for body movement during batting while the eye tracking system tracked the subject's eye movements while a ball is being pitched to the subject. Simultaneously, the subject's hands will be tracked with the body tracking system to monitor the movement and reaction to the pitched ball. The results may be correlated to assess the subject's ability to track a moving object (such as the baseball) in conjunction with a physical movement (swinging the bat). It will be appreciated that this invention may be applied to any sport or activity, as will be more fully described below.

An eye tracking system may measure and collect data, such as two-dimensional eye gaze positions, three-dimensional gaze positions, sample time, pupil diameter, whether the eye is open or closed, etc. More specifically, gaze information may include positions, duration, latency, accuracy, stability, smoothness, and other information related to a particular gaze, as well as fixations, saccades, smoother pursuit motion, convergence and divergence, scan path, dwell, blinks, etc.

In accordance with the present invention, any type of eye tracking system may used. For example, a non-contact, optical method may be used for measuring eye motion data that reflects light from the eye and then uses an optical sensor device, such as a video camera, to sense this reflected light. Such eye tracking systems may use the corneal reflection and the center of the pupil as features to track over time. A further example of a non-contact eye tracking system includes a dual-Purkinje eye tracker that uses reflections from the center of the cornea and the back of the lens as features to track.

In one embodiment, an eye tracking system may be video-based. That is, a camera may focus on one or both eyes and records their movement as the viewer looks at some kind of stimulus. An eye tracking system may use contrast to locate the center of the pupil, and then may use infrared and near-infrared non-collumnated light to create a corneal reflection. Generally, the vector between these two features may be used to compute gaze intersection with a surface after a simple calibration for an individual.

Examples of other eye tracking systems include those that attach to the eye, such as by a special contact lens with an embedded minor or magnetic field sensor. Then, the movement of the attachment may be measured with the eye movement. Alternatively, contact electrodes which measure electrical potential may be used. Such electrodes may be placed near the eye and measure the electric potential in the eye, where the cornea is positive relative to the retina.

The structure of eye tracking systems that may be used in conjunction with the present invention varies greatly; some are head-mounted, and some function remotely and automatically track the head during motion. A remote eye tracking system allows for ease of use in the present invention, when the body is in motion and is also being tracked. Generally, eye tracking systems use a sampling rate of at least 30 Hz. Although 50/60 Hz is most common, today many video-based eye trackers run at 240, 350 or even 1000/1250 Hz, which is needed in order to capture the detail of the very rapid eye movements.

Typically, eye movements may be divided into pursuits and saccades, while during fixations the eye gaze pauses in a certain position. The resulting series of pursuits, saccades, and fixations is called a scanpath. Most information through the eye is made available during pursuits and fixations, but not during a saccade. The central one or two degrees of the visual angle (the fovea) provide most of the fine detail and color information. The locations of fixations along a scanpath show what information loci on the stimulus were processed during an eye tracking session. On average, fixations last for around 200 ms during the reading of linguistic text, and 350 ms during the viewing of a scene. Preparing a saccade towards a new goal takes around 200 milliseconds. The input from peripheral field of view movement provides target detection, balance reference information, and spatial awareness of particular importance in sports, because the majority of action a subject observes when participating in an activity such as a sport occurs in the subject's non-primary gaze.

Scanpaths may be useful for analyzing cognitive intent, interest, and salience. Other biological factors may affect the scanpath as well. Eye tracking in HCl typically investigates the scanpath for usability purposes, or as a method of input in gaze-contingent displays, also known as gaze-based interfaces. Eye tracking may be used to differentiate between novice and expert behavior, as well as to train individuals for superior performance.

It will be further appreciated that any suitable body tracking system may be used in accordance with the present invention. Body tracking systems may include optical systems and non-optical systems. Exemplary optical systems may use passive markers, active markers, time-modulated active markers, semi-passive imperceptible markers, and markerless systems. Exemplary non-optical systems may include inertial, mechanical, and magnetic systems. For example, a force plate may be used to measure pressure, thereby tracking body movement of the subject.

Furthermore, tracking a subject's body movements may be accomplished using gesture recognition, which allows the gestures of the body components of the subject to be interpreted with the help of algorithms. Such methods of body tracking do not necessarily need tracking marks on the subject to interpret the gestures. Rather, various tools and methods may be used. For example, depth-aware cameras may generate a depth map of what is being seen through the camera and subsequently use this data to approximate a three-dimensional representation of the subject. In another example, stereo cameras may be used, which involves using two cameras to track the body components of the subject, and based on the locations of the cameras, a representation of the subject's body movement can be approximated. In such an example, a positioning reference (e.g., infrared emitters, etc.) may be used to determine the location of the cameras to each other.

In an additional embodiment, other related information of the subject, beyond eye and body movement may be tracked. Generally speaking, such information is referred to as physiological data herein. Physiological data may comprise, for example, balance, stability, and/or posture data. Other examples of physiological data may include biofeedback information that may be tracked and analyzed in conjunction with the eye tracking data and body tracking data. Exemplary biofeedback information may include plantar (foot) pressure, balance, sweat, temperature, heart rate, breathing rate, electrocardiogram (EKG) data, electroencephalogram (EEG) data, and the like.

FIG. 1 illustrates a system for eye and body tracking in accordance with the present invention, where a subject may perform various activities while being monitored by an eye tracking system and a body tracking system. In this example, eye tracking system 109 is illustrated as a pair of glasses or goggles, but it will be appreciated that any eye tracking system suitable for use in conjunction with a body tracking system may be used. For example, cameras that track the eye movement of a subject may be mounted using equipment in the general area of the subject. The eye tracking system chosen for a particular embodiment of the present invention may depend on what features of the eye are desirable to track, and may also depend upon what body features are desirable to track, since the eye tracking system must be compatible with the use of the particular body-tracking system, what other equipment is worn or used by the subject 101, and the like.

As seen in FIG. 1, a shirt 101 includes a chest tracking marks 103, a left arm tracking marks 105, and a right arm tracking marks 107. In FIG. 1, each of these tracking marks 103-107 has the appearance of a dark-colored cross shape. However, any type of marking may be used in conjunction with the present invention, and various types of marks may be particularly useful, or even necessary, for certain types of motion tracking systems. Moreover, in this example, each tracking mark 103-107 faces toward the front of the shirt 101 (that is, toward the front of a user wearing the shirt 101), so that the tracking marks 103-107 will appear in images taken by one more cameras in front of subject. The appearance and location of the tracking marks will depend upon the specific body tracking system used. Further, motion tracking systems used in accordance with the present invention need not utilize any type of tracking marks at all. Motion tracking systems that use transmitting markers, such as radio frequency markers, may be used in accordance with the present invention, as may motion tracking systems that use lasers, cameras, or other technologies to track an unmarked object or body part.

In the illustrated embodiment, the remainder of the shirt 101 other than the tracking marks 103, 105, 107 is relatively light, providing for good contrast between the tracking marks 103, 105, 107 and the shirt 101 itself. For example, the tracking marks 103, 105, 107 may be dark blue, brown, or black, while the remainder of the shirt 101 may be a bright white. This high contrast between the tracking marks 103, 105, 107 and the background of the shirt 101 will assist a body tracking system employing a camera to distinguish the tracking marks 103, 105, 107 from the background of the shirt 101. Moreover, the distinctive cross shape of the tracking marks 103, 105, 107 may assist a body tracking system to identify and distinguish these marks 103, 105, 107 from the background provided by the shirt 101. For example, the cross-shaped tracking marks 103, 105, 107 may be used with the body tracking system to distinguish a cross shape from other shapes imaged by a camera or cameras.

As will be appreciated by those of ordinary skill in the art, the tracking marks 103, 105, 107 can be applied to the shirt 101 using a variety of techniques. For example, the tracking marks 103, 105, 107 may be stitched to the shirt 101, adhered to the shirt 101 using any suitable adhesive, or woven or knitted into the material of the shirt 101. Further, the tracking marks 103, 105, 107 can be printed onto the shirt 101 using a pad printing technique. The tracking marks 103, 105, 107 also can be heat transferred onto the shirt 101, die-sublimated onto the shirt 101, or simply died into the material of the shirt 101.

Additionally in FIG. 1, the subject 100 is shown with an eye tracking system 109, which is used to track the eye movement of subject 100. In this example, subject 100 is participating in American football, and more specifically, is performing the action of catching football 111. As football 111 is thrown toward subject 100, the eye tracking system 109 tracks the eye movement of the subject, and the various tracking marks 103, 105, 107 comprising the body tracking system track the movement of each area of the body.

Figure 2:
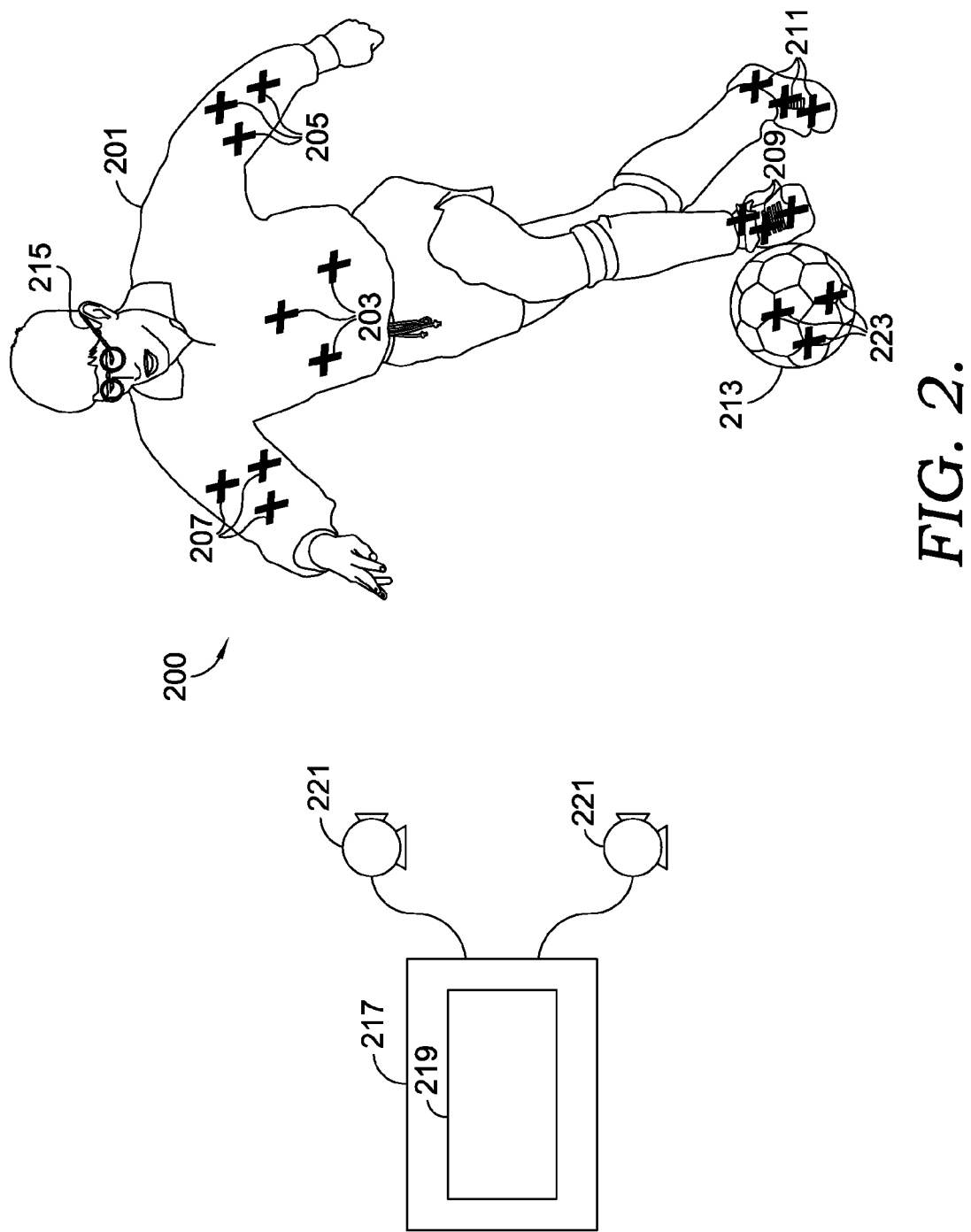
FIG. 2 illustrates another embodiment of a system for evaluating the performance of an individual in accordance with the present invention.

The use of an eye and body tracking system according to another embodiment of the invention is shown in FIG. 2. As seen in this figure, a subject 200 dons the shirt 201, with tracking marks 203, 205, 207 located at various locations on shirt 201. Here, subject 200 is participating in the activity of soccer, and is kicking a ball 213. Thus, additional tracking marks 209 and 211 are located on each foot of subject 200, in order to track the movement of each foot while subject 200 participates in various soccer activities. For example, subject 200 may perform a task such as taking a free kick.

More particularly, the subject 200 stands within the playing area defined for the body tracking system, which includes a pair of video cameras 221. Other components, such as a display device, may also be used a part of a system in accordance with the present invention. The body tracking system may also include a processing unit 217. The processing unit 217 may have a tracking mark recognition module 219. Tracking recognition module 219 may comprise a general purpose or special purpose computer having a processor, computer readable media having computer readable instructions embodied thereon, storage devices, input devices, output devices, network connections, etc. Further, tracking recognition module 219 may comprise a discrete uniform device, or a plurality of devices. The tracking mark recognition module 219 receives images from the cameras 221. From these images, the tracking mark recognition module 219 recognizes one or more tracking marks in the visual fields of the cameras 221, and determines the movement, if any, of the recognized tracking marks.

For example, the tracking mark recognition module 219 may employ an algorithm to recognize a tracking mark by distinguishing pixels having a particular color in an image obtained by a camera 221 from pixels in that image of other colors. Alternately, the tracking mark recognition module 219 may recognize a tracking mark by distinguishing the brightness of pixels of the tracking mark from the other pixels in an image obtained by the camera 221. Still further, the recognition module 219 may recognize a tracking mark by distinguishing pixels of a relatively uniform brightness, shade, or color that are arranged in a particular shape.

Once the tracking mark recognition module 219 recognizes one or more tracking marks, it then determines the movement of the recognized tracking marks. Algorithms for determining the movement of recognized images are well known in the art, and will not be discussed here in detail. For example, the tracking mark recognition module 219 may use a method of determining the three-dimensional position of an imaged tracking mark by comparing the position of a specific location on the mark in the image from one camera 221 with the position of the same location on the tracking mark in a simultaneous image from another camera 221, for the entire area of the tracking mark. Similarly, the movement and/or position of equipment, such as ball 213, may be tracked, for example by using marks 223.

With some embodiments of the invention, the tracking mark recognition module 219 may additionally determine movement of the user's extremities from the detected movement of the tracking marks. For example, using inverse kinematics, the tracking mark recognition module 219 may determine that a user has moved his or her right forearm based upon the detected rotation of one tracking mark (located at the user's wrist) about another stationary tracking mark (located at the user's elbow). The use of inverse kinematics is also well known in the art, and thus will not be described here in detail.

As can be seen in FIG. 2, the eye movement of subject 200 is tracked using an eye tracking system 215. Eye tracking system 215 may be connected to processing unit 217 of the body tracking system, or alternatively, the data collected by eye tracking system 215 may be collected at another location and may be compared to the body tracking data at a later time.

Figure 3:
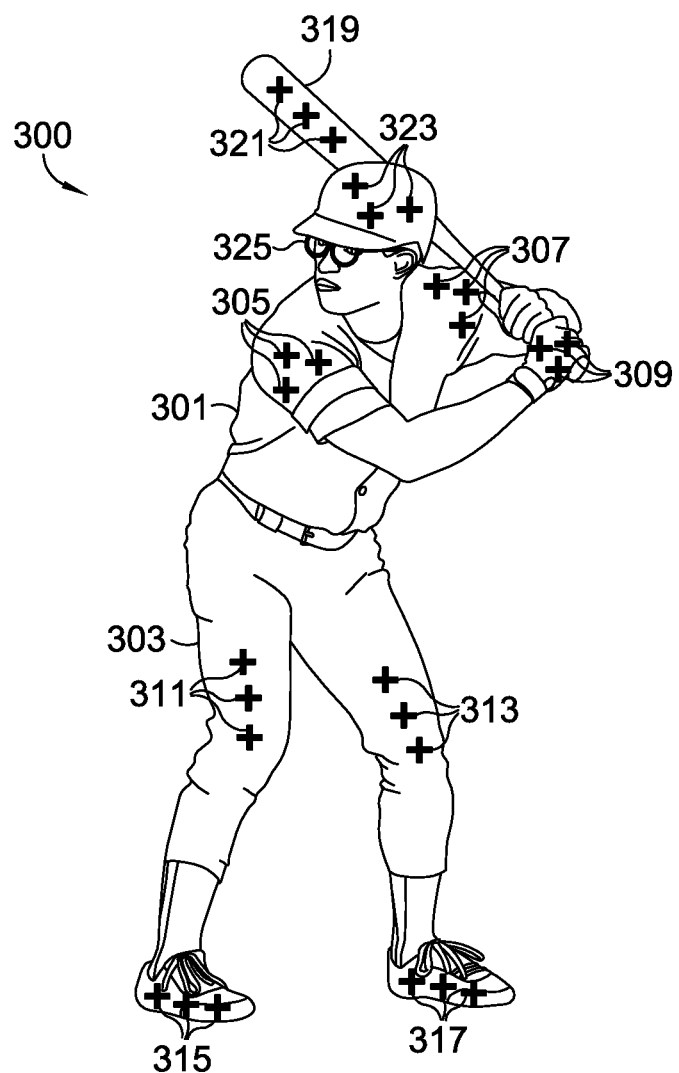
FIG. 3 illustrates a further embodiment of a system for evaluating the performance of an individual in accordance with the present invention.

Turning now to FIG. 3, another embodiment of the present invention is illustrated. More specifically, subject 300 is shown with a body tracking system and an eye tracking system while participating in baseball. Similar to the previous examples, the subject's eye movement may be tracked using eye tracking system 325

In this example, subject 300 is a batter anticipating a pitched baseball (not shown). As seen in FIG. 3, subject 300 is wearing a shirt 301 and pants 303 that both include various tracking marks. Shirt 301 includes a right shoulder tracking mark 305 and a left shoulder tracking mark 307. Pants 303 include tracking marks 311 on the right knee and tracking marks 313 on the left knee. Additionally, because the location of the subject's hands and the bat are important in hitting a baseball, each batting glove may include a tracking marks, such as marks 309 shown on the subject's right glove, where the subject is holding a bat 319 with tracking marks 321.

Similarly, the feet of subject 300 may be tracked using marks 315 on the right foot and marks 317 on the left foot). Tracking the movement of the subject's feet while the subject participates in the activity of hitting a baseball may be beneficial in analyzing the stride of the subject while swinging the bat 319. Further tracking marks 323 may be placed on the helmet of subject 300 to track the movement of the head of subject 300. The movement of subject may be captured using systems and methods in accordance with the present invention.

As in the previous examples, the number and location of the tracking marks for the body tracking system are intended only as examples, and should not be read as limiting the scope of the invention. Generally speaking, the greater the number of markers used the greater the accuracy of motion tracking of a given object or body part.

Figure 4:
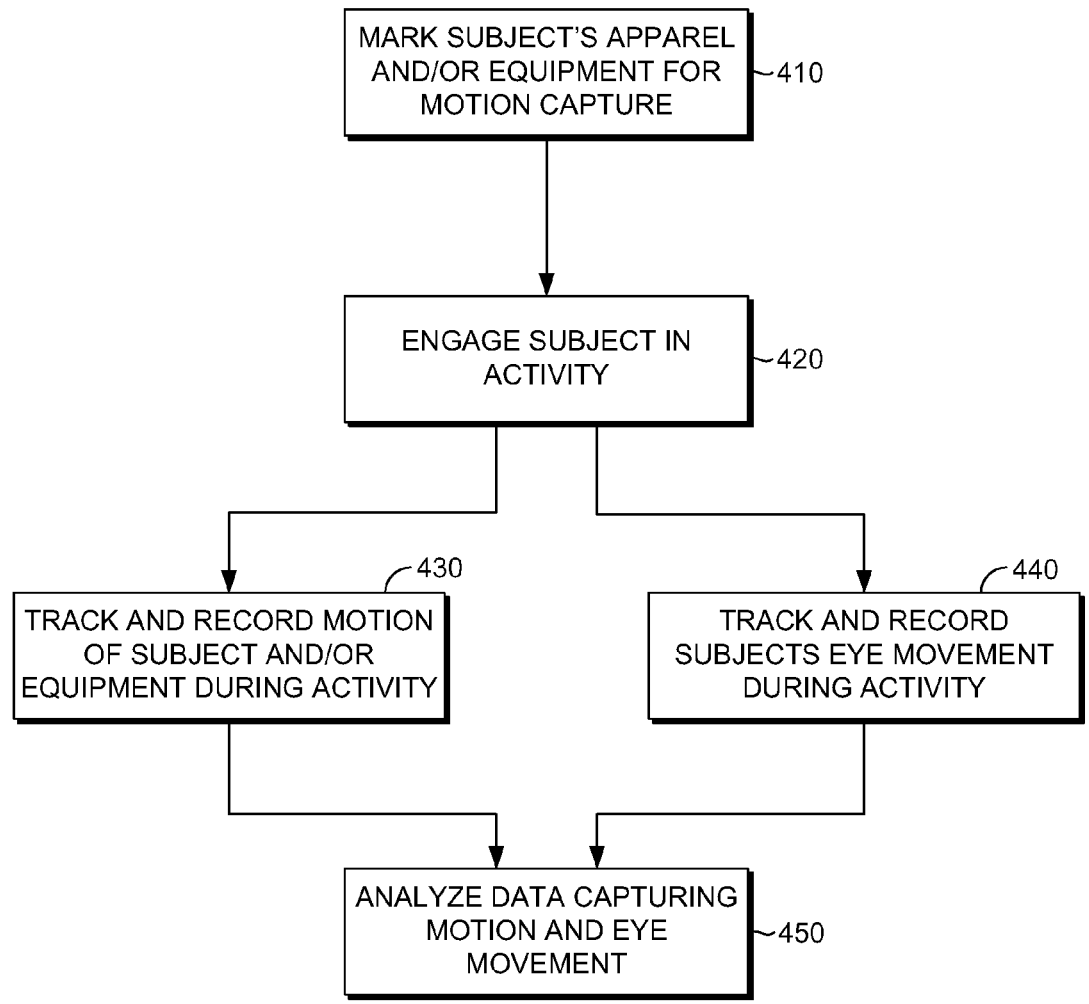
FIG. 4 illustrates a method for tracking the eye and body movement of a subject in accordance with an embodiment of the present invention.

The method of tracking eye and body movement of a subject, according to various embodiments of the invention, is illustrated in FIG. 4. As initially indicated by block 410, depending on the type of body tracking system used, the subject may be marked on various body components, and/or equipment used by subject may be marked. For example, the subject's apparel may be marked using tracking marks, such as those shown in FIGS. 1-3. The subject may also wear equipment that includes tracking marks, such as shoes, gloves, hats, etc. Alternatively, tracking marks may not be necessary if the body tracking system employs another method, such as gesture recognition, to track the body components of the subject.

Next at block 420, the subject is engaged in an activity. The activity of block 420 may be a task that is part of a given sport. Examples include any activity, but more particularly an activity that requires the eye to track an object, such as catching a football, blocking a soccer ball, hitting a baseball, etc. At this time, the subject's eye movement is also being tracked by, for example, an eye tracking system. As the subject is engaged in the activity, the subject's eye movement is tracked at block 440. At block 430, the subject's body and/or equipment is tracked while the subject is engaged in the activity. At block 450, the data collected from blocks 430 and 440 is analyzed to determine, for example, whether a correlation exists between the subject's eye and body movement. For example, the data points may be graphed together versus time over the duration of the activity for individuals with varying skill levels to distinguish between the visual behavior of individuals at different skill levels and to assist individuals in improving their skill level. Correlating the data over time may be used to show any gaps or weaknesses in eye-hand coordination of the subject, and may thus be used to further train the subject to improve any deficiencies. In collecting the tracking data, the data may be stored in any type of storage device and/or output device. Such a device may be connected to one or more of the tracking systems, or alternatively, the data may be transmitted to a remote storage or output device.

Figure 5:
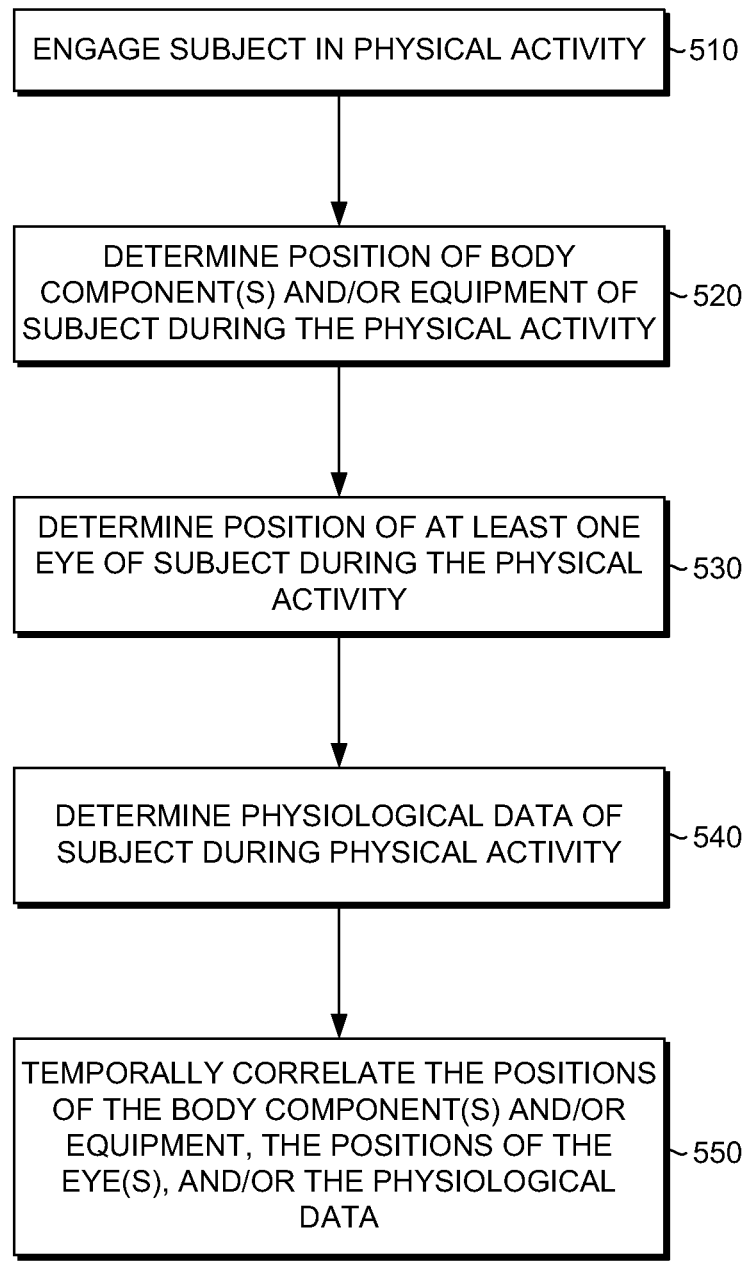
FIG. 5 illustrates a method for testing a subject's visual and cognitive abilities during physical activity in accordance with an embodiment of the present invention.

Turning now to FIG. 5, a method for testing a subject's visual and cognitive abilities during physical activity is shown in accordance with the present invention. Initially, as indicated at block 510, the subject is engaged in a physical activity. As discussed previously, the physical activity may be any sport or other activity, or any particular task related to a sport or activity. Next, at block 520 the position of the subject's body components and/or equipment is determined while the subject is engaged in the physical activity. More specifically, the position may be determined at a predetermined plurality of times. Further, one skilled in the art will appreciate that any number of body components of the subject may be tracked. For example, if the activity involved only the right arm of the subject, then the position of that one component may be the only body component tracked. Alternatively, if the specific activity involves the entire body, the position of each body component may be determined.

At block 530, the position of at least one eye of the subject is determined during the physical activity. At block 540, physiological data of the subject may be measured during the physical activity. As at block 520, the position of the at least one eye may be determined at a predetermined plurality of times during the activity and similarly, and similarly physiological data may be measured at a predetermined plurality of times during the activity. The plurality of times during which the eye position is determined and/or physiological data may be measured do not have to be the same plurality of times during which the body position is determined, nor need physiological data be measured at the same time eye position is determined. The positions of both the body components and/or equipment, the position of the eye(s), and/or the physiological data may then be temporally correlated, as indicated by block 550.

Figure 6:
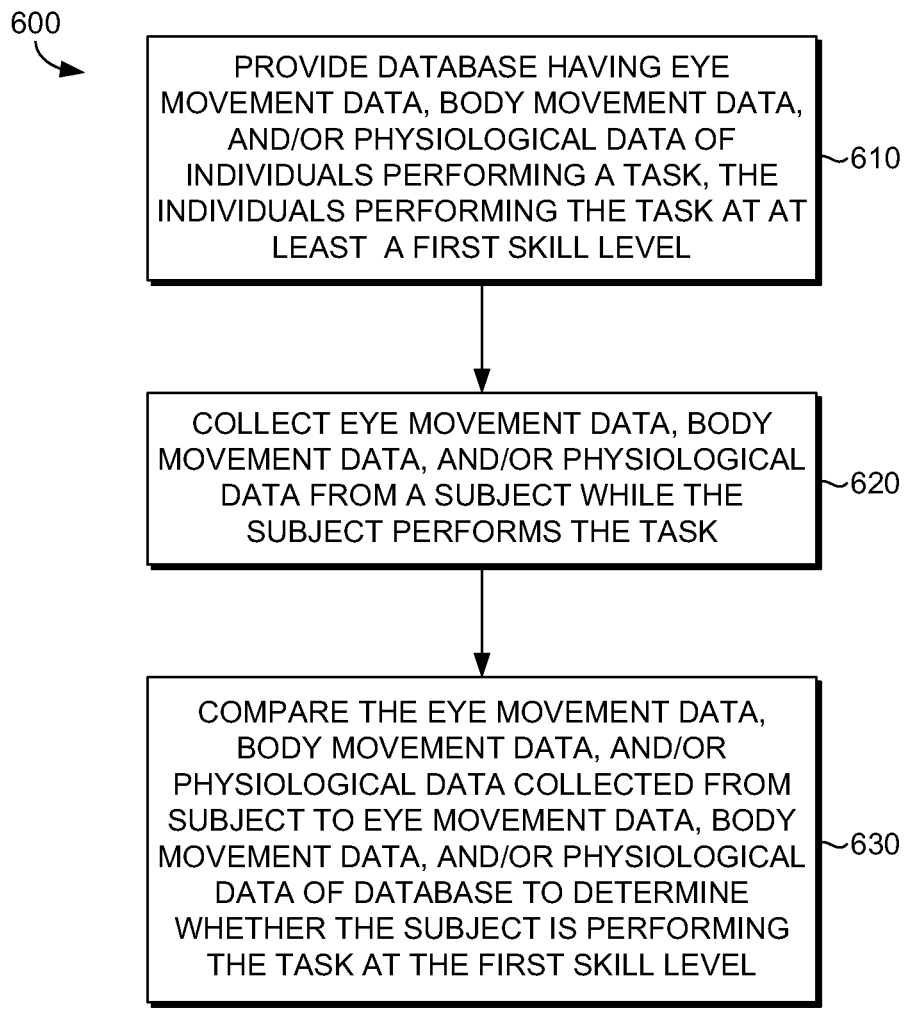
FIG. 6 illustrates a method for assessing the relative skills of an individual in accordance with the present invention.

Referring now to FIG. 6, a further method 600 in accordance with the present invention as illustrated. In step 610 a database having eye movement data, body movement data, and/or physiological data of individuals performing a task is provided. The database provided in step 610 may include other types of data, such as movement data for equipment used by individuals. In step 610, the database may comprise data collected from individuals having at least a first skill level. Step 610 may further comprise individuals having a variety of skill levels performing the task. For example, individuals identified as novices, intermediate, and/or expert levels of skill performing a given task may be collected into a database. The categorization of a given individual and the data corresponding to that individual at a particular skill level may be based upon an analysis of the collected data itself, or may be based upon an individual's objective performance level. For example, individuals participating at a professional level in a sport may be identified as experts, individuals performing at a collegiate level in a sport may be identified as intermediates, and individuals performing at a high-school level may be identified as novices. Of course, any variety of levels may be identified, and the labels attached to a given level need not be those described herein. For example, the levels of skill may, in fact, comprise all-star professional, professional, major college, college, junior college, major high school, high school, junior high school, other amateur, world-class elite, recreational, or any other kind of skill level identifier.

In step 620, eye movement data, body movement data, and/or physiological data may be collected from a subject while the subject performs the task. The data collected in step 620, as well as the data collected in step 610 and included in a database, may be collected using methods and systems such as those described herein, although other types of systems and methods may also be used. Further, the data collected in step 620, as well as the data provided in databases in step 610, may include varying types of eye movement data, body movement data, and/or physiological data, and need not include all three types of data, nor all types of categories of data potentially included in any one of those broad types. Further, other types of data, such as data describing the movement of equipment used by the subject.

In step 630, the eye movement data, body movement data, and/or physiological data collected from the subject may be compared to the eye movement data, body movement data, and/or physiological data of the database to determine whether the subject is performing the task at the first skill level. If other types of data are provided in step 610 and collected from subject in step 620, that data may also be compared in step 630. Of course, if multiple skill levels are included in the database provided in step 610, step 630 may determine which of a plurality of skill levels a subject is performing the task. Step 630 may potentially determine that a single individual performs the task at various skill levels for different types of data. For example, a subject may perform a task at an expert level for body movement data, but only at an intermediate level for eye movement data. Such an analysis may be advantageous in identifying areas for improvement for a subject.

Figure 7:
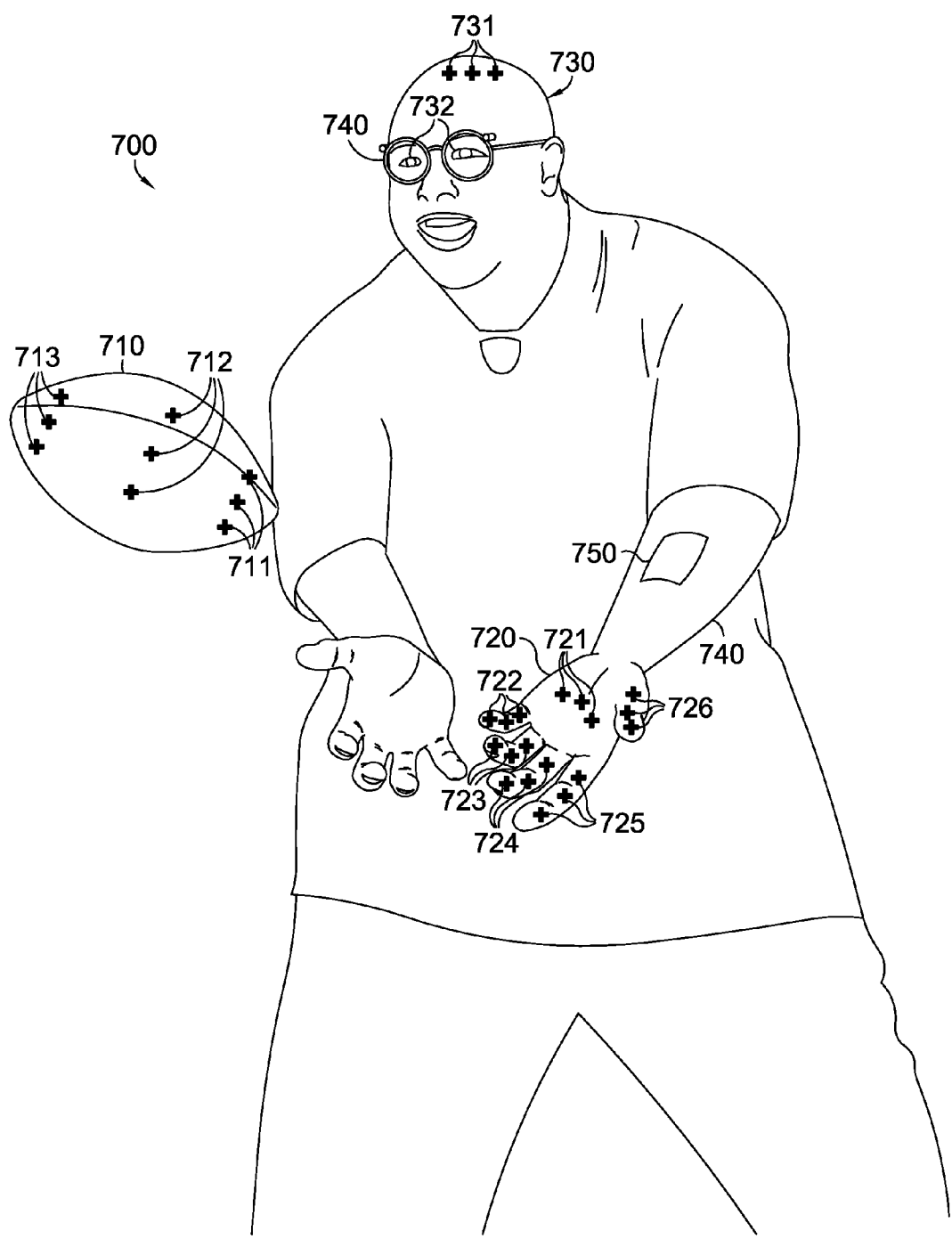
FIG. 7 illustrates another embodiment of a system for evaluating the performance of an individual in accordance with the present invention.

Referring now to FIG. 7, a further system 700 in accordance with the present invention for collecting movement data, eye movement data, and physiological data is illustrated. The task performed in FIG. 7 is a catching of an American football by a subject. Football 710 is illustrated moving generally towards a hand 720. Football 710 is illustrated having a first plurality of movement markers 711, a second plurality of movement markers 712, and a third plurality of movement markers 713. Of course, more or fewer movement markers than those illustrated in FIG. 7 may be utilized. The hand 720 may be marked at various locations with markers to facilitate the body movement tracking. For example, palm markers 721 may be provided on hand 720, in addition to first finger markers 722, second finger markers 723, third finger markers 724, and fourth finger markers 725, as well as thumb markers 726. While more or fewer markers may be utilized, generally speaking additional movement markers on hand 720 will result in a finer resolution of the movement of components of hand 720. While only a single hand 720 is illustrated with markers in this example, both hands may be marked and/or tracked during the task. Eye movement monitor 740 may be provided to monitor eyes 732. Of course, any type of eye movement monitor may be used in conjunction with the present invention although FIG. 7 illustrates a head mounted eye movement monitor 740. Further the position of head 730 may be monitored using tracking markers 731. Physiological data collection pad 750 may be adhered to a portion of subject 730, such as the subject's arm 740. Physiological data collection pad 750 may collect, for example, physiological data such as a pulse rate, perspiration rate, and/or other physiological data, some examples of which are described elsewhere herein. Of course, physiological data may be collected using apparatus other than pad 750. Pad 750 may communicate physiological data through a wired or wireless connection (not shown) to a computing device (not shown). The system illustrated in FIG. 7 may collect movement date, eye movement data, and physiological data while subject 730 catches football 710 using hand 720. Further, other parts of the body of subject 730 may be marked with motion markers, or body movement collection systems may be utilized that do not require markers such as those illustrated in FIG. 7. Systems such as system 700 may be used, for example, to evaluate task completion by a subject, for example whether the subject "looks the ball in" and "pops the head" on a catch.

Figure 8:
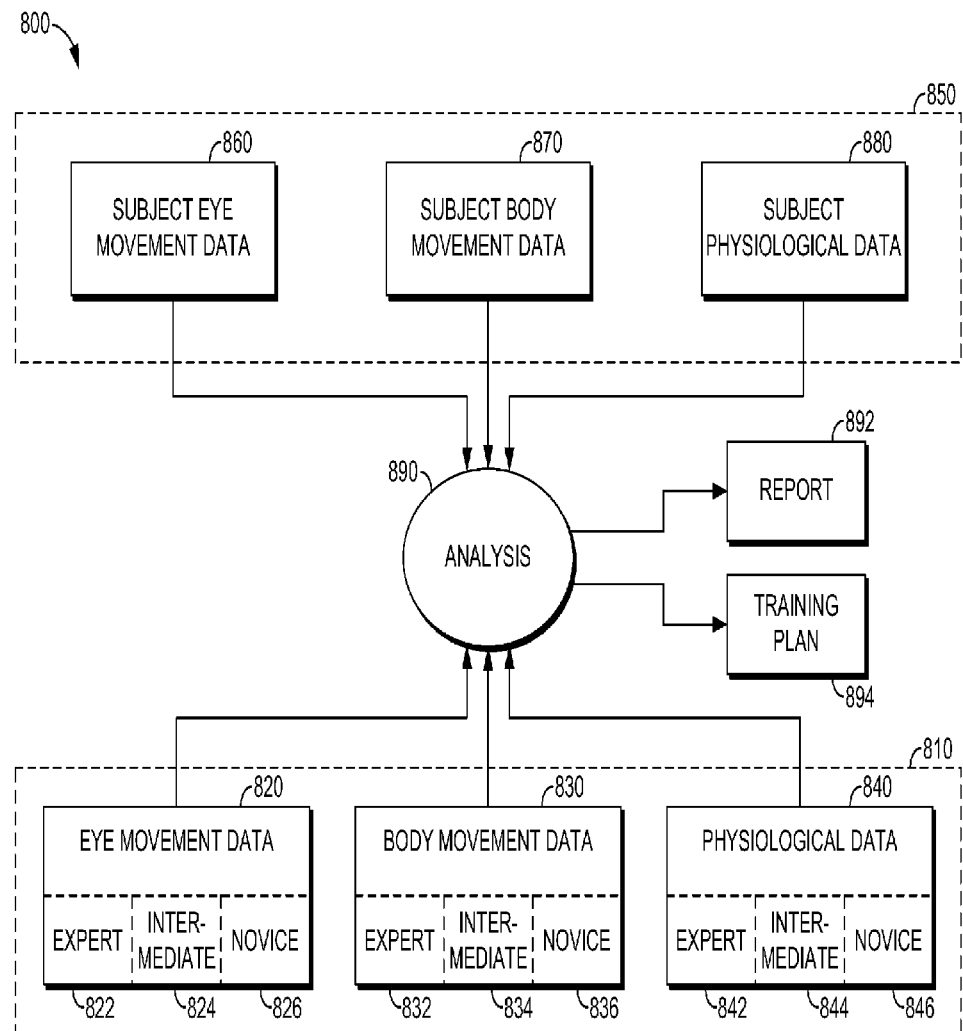
FIG. 8 illustrates a data analysis system for assessing the relative skills of an individual in accordance with the present invention.

Referring now to FIG. 8, a system 800 for collecting and analyzing data in accordance with the present invention is illustrated. A database 810 may contain data collected from subjects having various skill levels while performing a sport activity, or task. Eye movement data 820 in database 810 may be subdivided into an expert level 822, and intermediate level 824, and a novice level 826, although other levels may be used as well. Body movement data 830 in database 810 may similarly be divided into an expert level 832, an intermediate level 834, and a novice level 836. Physiological data 840 in database 810 may be divided into an expert level 842, an intermediate level 844, and a novice level 846, although other levels may of course be used. As explained above, for example with regard to FIG. 6, skill levels other than those illustrated in FIG. 8 may be used, as the designations of "expert," "intermediate," and "novice" are used for the sake of convenience, but may not be readily applicable to search in types of tasks.

Data collection component 850 may be used to collect data from a subject while performing a sport, activity or task. Data collection component 850 may comprise, for example, systems such as those illustrated and/or described above, although other systems may also be utilized. Data collection component may provide eye movement data of a subject 860, body movement data of a subject 870, and physiological data of a subject performing the sport, activity, or task. Analysis component 890 may compare the data from data collection component 850 to data in database 810. Analysis component may provide a report 892 identifying and/or classifying the level of performance of a subject for any given type of data (such as eye movement, body movement, and/or physiological) or overall. Analysis component 890 may also provide a training plan for a subject. Training plan 894 may identify areas for subject to attempt to improve and may further provide a series of activities that may be performed by subject to attempt to improve subject's performance. Analysis component 890 may comprise software operating on any type of computer having a processor and computer readable media to perform a comparison between the subject's data and the data stored in database component 810.

Figure 9:
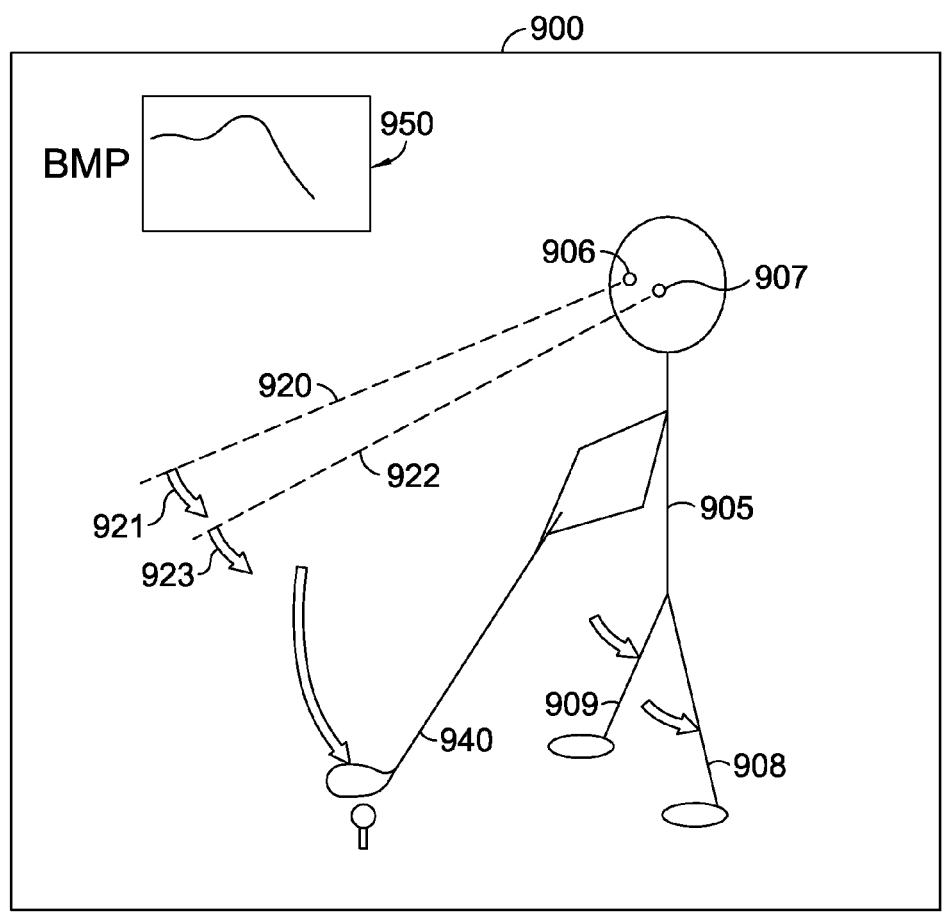
FIG. 9 illustrates a display of data in accordance with the present invention.

Referring now to FIG. 9 an analysis display 900 that may be used in accordance with the present invention is illustrated. Analysis display 900 provides one illustration of an exemplary display of collected data in accordance with the present invention. Analysis display 900 may provide body movement data graphically illustrating the movement of a subject 905 and equipment such as golf club 940 utilized by subject in a task, such as striking a golf ball from a tee. Display 900 may show the movement of subject 905 and subject's body parts, such as first leg 908 and second leg 909, as well as equipment such as golf club 940 while performing the task in this example striking a golf ball. Movement is indicated as arrows in FIG. 9, but display 900 may comprise moving animation. Similarly, display 900 may illustrate the movement, direction, and/or focus of the first eye 906 and second eye 907 of subject 905. As illustrated in the example of FIG. 9, first eye 906 has a gaze angle 920 illustrated by a dotted line, with a movement indicated by an arrow, while second eye 907 has a gaze angle identified by dotted line 922 moving as indicated by another arrow. While arrows are used to illustrate movement of gage angles, display 900 may comprise moving animation. Also illustrated in display 900 is physiological data display 950, in the present example beats per minute of the heart of subject 905. Display 900 provides an example of one way in which data collected in accordance with the present invention may be presented to an expert for analysis or to subject himself/herself to better enable subject to improve performance through training, etc.

The present invention has been described herein in relation to particular embodiments, which are intended in all respects to be illustrative rather than restrictive. Alternative embodiments will become apparent to those of ordinary skill in the art to which the present invention pertains without departing from its scope.

The invention claimed is:

1. A method for testing or training the eye and body movement of a subject while the subject performs a task, the method comprising:
    tracking the subject's eye movement while the subject performs the task to produce eye movement data associated therewith;
    tracking the subject's body movement while the subject performs the task to produce body movement data associated therewith;
    recognizing a gesture from the body movement data; and
    determining a correlation between the subject's eye movement data and the gesture.

2. The method of claim 1, wherein the subject's eye movement is tracked by an eye tracking system.

3. The method of claim 1, wherein the subject's body movement is tracked by a body tracking system.

4. The method of claim 3, wherein tracking the subject's body movement comprises generating one or more depth maps of the subject's body.

5. The method of claim 3, further comprising:
    collecting physiological data while the subject performs the task to produce physiological data associated therewith; and
    determining a correlation between the subject's physiological data and the subject's eye movement data and the subject's body movement data.

6. The method of claim 3, wherein the body tracking system one of an optical system and a non-optical system.

7. The method of claim 1, wherein determining a correlation between the subject's eye movement and the subject's body movement includes plotting the eye movement and body movement versus time.

8. The method of claim 1, further comprising:
    storing the eye movement data and the body movement data on a storage device.

9. The method of claim 1, further comprising:
    sending the eye movement data and the body movement data to an output device.

10. A system for testing or training the eye and body movement of a subject, the system comprising:
    an eye tracking system that tracks the eye movement of a subject, wherein the eye tracking system collects eye movement data associated with the subject's eye movement;
    a body tracking system that tracks the body movement of a subject by tracking one or more markers on the subject's apparel, wherein the body tracking system collects body movement data associated with the subject's body movement; and
    a computing device that analyzes the eye movement data and the body movement data.

11. The system of claim 10, further comprising:
    a physiological data collection system, wherein the physiological data collection system collects physiological data associated with the subject's physiological condition; and wherein
    the computing device further analyzes the physiological data.

12. The system of claim 10, wherein the eye tracking system tracks the subject's eye movement by tracking the lens of at least one of the subject's eyes.

13. The system of claim 10, wherein the one or more markers are at least one member of a group comprising passive markers, active markers, time-modulated active markers, and markers imperceptible to a human eye.

14. The system of claim 10, wherein the body tracking system comprises one or more stereo cameras.

15. The system of claim 10, further comprising determining a positioning reference for the subject's body using infrared emitters.

16. The system of claim 15, wherein the body tracking system uses two stereo cameras to track the subject's body movement, and based on locations of the stereo cameras, the body tracking system approximates a representation of the subject's body movement.

17. The system of claim 10, further including a storage device on which the eye movement data and the body movement data is stored.

18. A method for testing or training a subject's visual and cognitive abilities during physical activity, the method comprising:
    engaging the subject in a physical activity;
    determining the position of at least one body component of the subject during the physical activity at a first predetermined plurality of times;
    determining the position of at least one eye of the subject during the physical activity at a second predetermined plurality of times;
    determining physiological data for the subject based on balance, stability, or posture of the subject; and
    temporally correlating the positions of the at least one body component at the first predetermined plurality of times and the positions, the at least one eye at the second predetermined plurality of times, and the physiological data during either the first or second predetermined plurality of times.

19. The method of claim 18, wherein tracking the subject's eye movement includes tracking the lens of at least one of the subject's eyes.

20. The method of claim 18, further comprising:
    storing the positions of the at least one body component and the positions of the at least one eye on a storage device.

* * * * *